United States Patent [19]

Smith et al.

[11] Patent Number: 5,494,590
[45] Date of Patent: Feb. 27, 1996

[54] METHOD OF USING ANTICOAGULANT SOLUTION IN BLOOD SEPARATION

[75] Inventors: Ward C. Smith, Toms River, N.J.; Richard J. Carroll, Syracuse, N.Y.

[73] Assignee: Becton Dickinson, Franklin Lakes, N.J.

[21] Appl. No.: 897,305

[22] Filed: Jun. 11, 1992

[51] Int. Cl.$^6$ ................................................ B01D 21/26
[52] U.S. Cl. ...................... 210/782; 210/787; 210/789; 435/2; 436/177
[58] Field of Search ................................ 210/782, 787, 210/789, 513, 514, 515, 516; 422/101, 102; 436/177; 435/2; 424/533

[56] References Cited

U.S. PATENT DOCUMENTS

| | | | |
|---|---|---|---|
| 3,847,738 | 11/1974 | Brake et al. | 435/2 |
| 3,852,194 | 12/1974 | Zine, Jr. | 210/516 |
| 4,147,628 | 4/1979 | Bennett et al. | 210/516 |
| 4,190,535 | 2/1980 | Luderer et al. | 210/516 |
| 4,356,172 | 10/1982 | Nakao et al. | 435/2 |
| 4,457,782 | 7/1984 | Honda et al. | 210/516 |
| 4,500,309 | 2/1985 | Diederich et al. | 210/646 |
| 4,534,798 | 8/1985 | Honda et al. | 210/510.1 |
| 4,640,785 | 2/1987 | Carroll et al. | 210/782 |
| 4,695,460 | 9/1987 | Holme | 435/2 |
| 4,867,887 | 9/1989 | Smith | 210/782 |
| 4,925,665 | 5/1990 | Murphy | 435/2 |
| 4,957,638 | 9/1990 | Smith | 210/782 |
| 4,961,928 | 10/1990 | Holme et al. | 435/2 |
| 5,248,506 | 9/1993 | Holme et al. | 435/2 |

FOREIGN PATENT DOCUMENTS

| | | |
|---|---|---|
| 63-015161 | 1/1988 | Japan. |
| 62-276460 | 5/1988 | Japan. |

OTHER PUBLICATIONS

Holodniy, M., et al., "Inhibition of Human Immunodeficiency Virus Gene Amplication by Heparin", Journal of Clinical Microbiology, 29, 676–679, (Apr. 1991).

Walter, H., et al., "Differential Effect of pH on the Density and Volume of Rat Reticulocytes and Erythrocytes", Cell Biophysics, 16, 139–148, (1990).

Reinhart, W. H., et al., "Influence of blood withdrawal and anticoagulant on clotting activity, hematologic data, and certain rheologic measurements", J. Lab. Clin. Med., 115, 98–103 (1990).

Letwin, B. W., et al., "An Improved Clonal Excess Assay Using Flow Cytometry and B–Cell Gating", Blood, 75, 1178–1185, (Mar. 1990).

Miller, C., et al., "Effects of Storage Conditions on Lymphocyte Phenotypes From Healthy and Diseased Persons", Journal of Clinical Laboratory Analysis, 3, 296–300, (1989).

Lombarts, A., et al. "Recognition and Prevention of Pseudothrombocytopenia and Concomitant Pseudoleukocytosis", A.J.C.P., 89, 634–639, (1988).

Patrick, C., et al., "Collection and Preparation of Hematopoietic Cells for Cell Marker Analysis", Laboratory Medicine, 15, 659–665, (Oct. 1984).

*Primary Examiner*—John Kim
*Attorney, Agent, or Firm*—Hoffmann & Baron

[57] ABSTRACT

An anticoagulant solution of sodium citrate for use in blood chemistry-related techniques and apparatus is disclosed. The anticoagulant solution should include an effective concentration of sodium citrate sufficient for preventing the coagulation of a sample of blood employed in the technique or added to the apparatus. The sodium citrate-based anticoagulant solution should have a pH ranging from above 6.0 to about 8.5 and a sodium citrate concentration preferably ranging from about 0.05M to about 0.2M.

10 Claims, 1 Drawing Sheet

U.S. Patent      Feb. 27, 1996      5,494,590
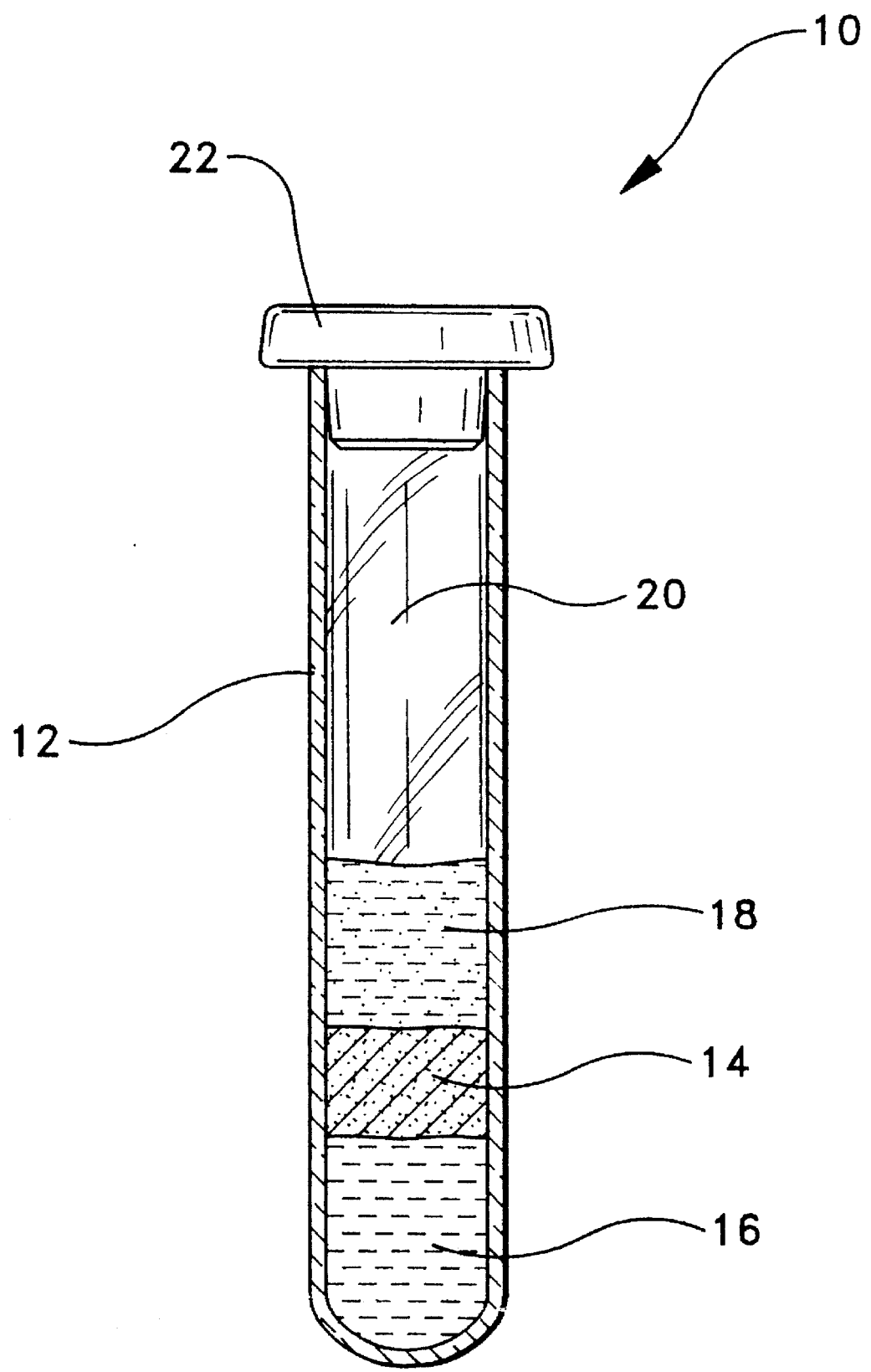

METHOD OF USING ANTICOAGULANT SOLUTION IN BLOOD SEPARATION

BACKGROUND OF THE INVENTION

1. Field of Invention

The present invention generally relates to blood chemistry laboratory techniques and apparatus. More particularly, the present invention relates to methods for separating mononuclear cells, such as lymphocytes and monocytes, from whole blood specimens, especially assemblies or methods which maintain blood in an anticoagulated state prior to partitioning the sample into discrete layers using centrifugation. Additionally, the present invention relates to blood separation assemblies which provide a high recovery of mononuclear cells without significant contamination by red blood cells.

2. Description of the Prior Art

Considerable research has been conducted in recent years to develop improved methods and devices for separating mononuclear cells, such as lymphocytes and monocytes, from whole blood. Effective separation and isolation of these cells is often critical to various clinical assays as well as to research laboratory protocols. Consequently, a variety of blood collection/separation tubes have been developed.

For example, one currently available blood separation device includes a blood collection tube containing an aliquot of a Newtonian gel and an aliquot of a liquid density medium, such as Ficoll-Paque™. The Newtonian gel acts as a barrier between the liquid density medium and a sample of anticoagulated whole blood which is placed in the tube above the gel prior to centrifugation. When the tube is subsequently centrifuged, the liquid density medium acts to separate the mononuclear cells from the other blood components. The separation occurs because the specific gravity of the density medium is greater than the specific gravity of the mononuclear cells but less than the specific gravity of the other blood components.

The aforementioned device and method works well where the tube is immediately centrifuged upon receipt of the whole blood sample but cannot be utilized as an effective separation means where the blood sample is placed in the tube and must be shipped elsewhere for subsequent centrifugation, isolation and analysis. The reason for this limitation is that both the Newtonian gel and the liquid density medium are flowable liquids and will not retain their respective positions in the tube due to movements occurring during shipping. As a result, the blood sample will mix with the density medium during shipping, thereby diluting it. Dilution of the medium adversely affects the proper separation of the blood sample upon subsequent centrifugation at the laboratory. Such dilution is especially problematic in laboratory studies where contamination of the mononuclear layer by red blood cells must be minimized.

Consequently, other blood separation devices have been developed. For example, one of these devices is a blood separation tube in which a porous foam-like plug is deployed above a liquid density separation medium. The plug functions as a "baffle" for preventing a blood sample introduced into the tube from mixing with the separation medium prior to centrifugation. Although the plug is constructed with a porosity suitable for allowing migration of red blood cells and separation medium therethrough during centrifugation, the plug design prevents the blood sample from interfacing with the separation medium prior to centrifugation, thereby facilitating a cleaner separation of the mononuclear cell layer.

Another currently available blood separation device utilizes a non-Newtonian, thixotropic gel. This gel is positioned within a blood collection tube in order to form a stable barrier between the liquid density medium and the blood sample prior to centrifugation. For example, U.S. Pat. No. 4,867,887 to Smith discloses several embodiments of a separation device utilizing a thixotropic gel. In one such embodiment, a blood collection tube includes a layer of a Newtonian gel positioned in the bottom of the collection tube. A thixotropic gel is temporarily positioned immediately above the Newtonian gel in order to prevent the Newtonian gel from mixing with the blood sample prior to centrifugation. A space is provided above the thixotropic gel suitable for allowing placement of a blood sample into the tube prior to centrifugation.

Upon the addition of an anticoagulated whole blood sample and subsequent centrifugation, the thixotropic gel moves to the bottom of the tube, thereby displacing the Newtonian gel. Since the specific gravity of the Newtonian gel is less than the specific gravity of the thixotropic gel, the Newtonian gel moves to a new position above the thixotropic gel where it mixes with the blood sample and acts as a density separation medium much like the liquid density medium, Ficoll-Paque™. Red blood cells, which have the highest specific gravity of any of the components in whole blood, are pelleted along with the granulocytes to the bottom of the tube immediately below the thixotropic layer. The mononuclear cells form a layer immediately above the Newtonian gel, thereby rendering an effectively isolated layer of cells to be removed for clinical analysis or other laboratory manipulations.

A further embodiment disclosed in U.S. Pat. No. 4,867,887 to Smith involves a similar configuration for a blood separation device including a collection tube containing a density gradient material, a Newtonian gel, a thixotropic gel and an aliquot of an anticoagulant/cell-sustaining solution. Prior to the addition of any blood sample or centrifugation, the density gradient material and the Newtonian gel are positioned in the bottom portion of the tube immediately below the thixotropic gel. An aliquot of anticoagulant/cell-sustaining solution is placed into the tube above the thixotropic gel which serves as a temporary barrier to isolate the solution from the other components in the tube. A space is provided within the tube above the solution. The space is suitable for allowing the placement of an anticoagulated blood sample into the tube prior to centrifugation.

After a sample has been received in the tube and centrifugation is performed, the red blood cells and granulocytes are pelleted to a position at the bottom of the tube immediately below the thixotropic gel layer. The density gradient material moves to a new position above the thixotropic gel where it mixes with the blood sample as well as the anticoagulant/cell-sustaining solution in order to perform a separation function. The density gradient material includes both a light and a heavy phase which separate into two layers in order to sandwich the Newtonian gel layer therebetween. The mononuclear cells form a layer immediately above the lighter phase of the density gradient and are subsequently removed for analysis.

In both of the embodiments disclosed by Smith, the thixotropic gel acts as a barrier to isolate the other components of the separation device from one another prior to centrifugation. In the second embodiment, the Newtonian gel is not used as a barrier nor a separation medium since the thixotropic gel and the density gradient material perform these functions, respectively. The Newtonian gel alternatively performs a quality control function in that it provides a sticky surface to retain any residual red blood cells located near the mononuclear cell layer after centrifugation, thereby facilitating removal of the mononuclear cells and limiting any contamination with residual red blood cells.

U.S. Pat. No. 3,852,194 discloses a simpler blood separation device utilizing a thixotropic gel material having a specific gravity in between that of mononuclear cells and other components of whole blood, such as red blood cells and granulocytes. Consequently, the thixotropic gel functions as a separation medium rather than performing a barrier function as in the '887 patent to Smith.

Other blood separation devices are designed for blood collection as well as separation. For example, various direct draw blood collection containers are currently available. Some of these are designed for undergoing subsequent centrifugation, thereby eliminating the need for mechanically transferring a blood sample to a different container prior to inducing separation via centrifugation.

The blood collection and/or separation tubes mentioned above are only a few of many such containers known to those skilled in the art. Regardless of the type of container employed to perform the collection and/or separation function, preventing contamination of the mononuclear cell layer with red blood cells remains a key concern for diagnostic studies which demand minimal levels of RBC contamination.

Various anticoagulants have been used in blood collection/separation devices either alone or in conjunction with a cell-sustaining solutions in order to preserve the blood sample in an uncoagulated state for a period of time prior to centrifugation and analysis. For example, some common anticoagulants include sodium heparin, $K_3EDTA$ and sodium citrate. In particular, sodium citrate solutions have been used for many years as anticoagulants. For example, current requirements for gene amplification technologies, such as the polymerase chain reaction, recommend the use of sodium citrate for performing an anticoagulation function in whole blood. See Holodniy, M.; Kim, S.; Katzenstein, D.; Konrad, M.; Groves, E.; Merigan, T. C.; "Inhibition of Human Immunodeficiency Virus Gene Amplification by Heparin", J. Clin. Microbiol. 29:676–679 (1991).

It is known that calcium plays a key role in the blood coagulation cascade. Sodium citrate solutions prevent the participation of calcium in blood coagulation. Typically, these sodium citrate solutions are added to freshly collected whole blood to prevent coagulation. Subsequently, calcium can be added back to the whole blood suspension to induce subsequent coagulation when desired.

Sodium citrate is a particularly advantageous anticoagulant as it provides good buffering capabilities over a range of pH. In particular, the buffering capability of sodium citrate is attributable to three carboxyl groups present on the corresponding acid of the compound. Since sodium citrate is the corresponding sodium-based salt of citric acid, it is actually the citric acid/sodium citrate combination that actually functions to perform the buffering chemistry.

As mentioned above, citric acid (hydroxytricarboxylic acid) has 3 carboxyl groups and consequently 3 pKa's. The first pKa appears at a pH of about 3.06. The second pKa appears at a pH of about 4.74. The third pKa appears at a pH of about 5.4. Accordingly, sodium citrate performs its most effective buffering functions at these pH values and is especially useful in performing buffering functions when added to in vitro cell suspensions. Consequently, sodium citrate has been used as an anticoagulant in a variety of blood separation devices due to its buffering capability over a range in pH.

In particular, citrate has been commonly used as an anticoagulant in three types of solutions. The first type of solution is referred to as buffered sodium citrate. The second type of solution is typically referred to as CPD solution or citrate-phosphate-dextrose. The third type is denoted as ACD or acid-citrate-dextrose. The citrate ion concentration in these solutions is typically greater than the concentration needed to perform an anticoagulation function. Examples of these three solutions as well as other currently available citrate-based anticoagulant solutions are included in the following table.

CITRATE-BASED ANTICOAGULANT FORMULATIONS

| Buffered Sodium Citrate | | |
|---|---|---|
| Per Liter: | | |
| 0.109 Molar | 0.129 Molar | |
| 24.7 gm | 32.0 gm | $Sodium_3$ $Citrate.2H_2O$ |
| 4.42 gm | 4.2 gm | Citric $Acid.H_2O$ |
| pH 6.1 | | |
| Acid Citrate Dextrose | | |
| Per Liter: | | |
| ACD-A | ACD-B | |
| 0.2 gm (Antimycotic) | 0.2 gm | Potassium Sorbate |
| 22.0 gm | 13.2 gm | $Sodium_3$ $Citrate.2H_2O$ |
| 24.5 gm | 14.7 gm | $Dextrose.H_2O$ |
| 8.0 gm | 4.8 gm | Citric $Acid.H_2O$ |
| pH 5.05 | pH 5.1 | |
| CPD (CPDA-1 Contains 0.275 gm ADENINE) | | |
| Per Liter: | | |
| 0.2 | | Potassium Sorbate |
| 26.3 gm | | $Sodium_3$ $Citrate.2H_2O$ |
| 3.27 gm | | Citric $Acid.H_2O$ |
| 2.22 gm | | Monobasic Sodium $Phosphate.H_2O$ |
| 25.5 gm | | $Dextrose.H_2O$ |
| pH 5.8 | | |
| Alsever's Solution | | |
| Per Liter: | | |
| 8.0 gm | | $Sodium_3$ $Citrate.2H_2O$ |
| 22.6 gm | | $Dextrose.H_2O$ |
| 4.2 gm | | Sodium Chloride |
| | | Citric Acid to Adjust pH to 6.1 |
| LeucoPREP ™ Citrate | | |
| Per Liter: | | |
| 0.10 Molar | | |
| 29.4 gm | | $Sodium_2$ $Citrate.2H_2O$ |
| 0.27 gm | | Citric $Acid.H_2O$ |
| pH 7.0 | | |

Typically, the highest pH at which sodium citrate has been used in the past as an anticoagulant has been 6.0. This pH level constitutes the upper limit within which sodium citrate has been utilized as an effective buffer. In most blood separation/collection tube devices used for separating mononuclear cells from whole blood, any sodium citrate solution incorporated therein to perform an anticoagulation function has had a pH ranging from about 5.05 to about 6.0. In the past, this range in pH has been the most preferential.

Unfortunately, the use of various sodium citrate anticoagulant formulations have not provided satisfactory results when used in many of the currently available blood separation/collection containers, especially those which utilize a thixotropic gel as a barrier or a separation means. In particular, the resulting layer of mononuclear cells appearing after centrifugation is contaminated to an unacceptable level with red blood cells when any of the above-mentioned sodium citrate-based formulations are used as anticoagulants. This contamination is very problematic with respect to certain laboratory manipulations requiring a high degree of purity in the mononuclear cell fragment.

For example, the mononuclear layer of cells contain lymphocytes which play a major part in the body's immune system. They are harvested and used in research activities directed toward defining the molecular biology and cellular interactions of immune mechanisms. Additionally, the analysis of lymphocytes is important in infectious disease detection, in cancer and auto-immune disease research, and, is fundamental to monoclonal antibody technology.

Due to the significance of lymphocytes, isolation of these cells from human blood is necessary for a variety of diagnostic assays. Included in such assays are functional assays, paternity testing and tissue typing. Additionally, an assessment of immune competency can be accomplished through analysis of lymphocyte sub-types and ratios. Accurate assessments of immune competency is significant in the diagnosis of AIDS and is prognostic in many other chronic and often terminal infections. Cellular assays are also utilized to monitor immune regulating drugs employed in cancer therapy. Additionally, accurate determination of lymphocyte surface markers is critical for histocompatibility determinations.

As a consequence of the foregoing, it is necessary that methods and apparatus for providing a highly effective separation of mononuclear cells from the other components in whole blood are available to clinicians as well as research investigators. If the mononuclear cells are contaminated to an unacceptable level with red blood cells or granulocytes, many of the foregoing objectives cannot be easily achieved.

For example, it has been discovered that whole blood samples added to blood separation devices utilizing thixotropic gels in conjunction with sodium citrate-based anticoagulant solutions, as mentioned above, do not perform well. Adequate separation and isolation of mononuclear cells for many applications cannot be achieved due to contamination with red blood cells and granulocytes. Since red blood cells and granulocytes must migrate through the thixotropic gel layer during centrifugation, it has been postulated that the currently available sodium citrate-based anticoagulant solutions have somehow undesirably interacted with the migration of red blood cells, resulting in an ineffective separation of the red blood cell component from the mononuclear layer.

It is therefore an object of the present invention to provide a novel anticoagulant solution for use in blood chemistry-related techniques performed in laboratories and clinics, as well as devices employing the same.

It is also an object of the present invention to provide a new sodium citrate-based anticoagulant solution for use in blood separation/collection containers, whereby improved separation of the mononuclear cell layer is achieved upon separation by centrifugation.

It is a further object of the present invention to provide a new blood separation assembly including a thixotropic gel layer in conjunction with a sodium citrate-based anticoagulant solution, whereby an improved separation of the mononuclear cell layer from the remainder of a blood sample is achieved upon centrifugation of the assembly.

SUMMARY OF THE INVENTION

The present invention is a novel anticoagulant solution for use in blood chemistry-related techniques and devices, especially blood collection and separation assemblies. The solution of the present invention is particularly useful in blood separation assemblies which are capable of centrifugally separating lymphocytes and monocytes from heavier phases of a sample of whole blood or, alternatively, from a pretreated cell fraction of blood. More particularly, the anticoagulant solution of the present invention is especially useful when employed in a blood separation assembly including a container, preferably a blood collection tube, which has a thixotropic gel-like substance positioned within it. The solution is placed in the tube above the thixotropic gel. The gel can serve as a barrier to isolate the solution from the remainder of the components of the tube or as a density separation medium, or both.

The anticoagulant solution of the present invention should include an effective concentration of sodium citrate sufficient for preventing the coagulation of a sample of blood when such a sample is added to the container. In particular, the sodium citrate-based anticoagulant solution should have a pH ranging from above 6.0 to about 8.5 and a sodium citrate concentration ranging from about 0.05M to about 0.2M.

As previously mentioned, the anticoagulant solution of the present invention may also be incorporated into a particular blood separation assembly, thereby providing for a new and useful version of such a device. Such devices typically include a container having an open and a closed end. The container is preferably a blood separation tube. The container may include a first layer of a thixotropic gel-like substance positioned within it at a first position. The anticoagulant solution of the present invention should be positioned in the container at a second position which is closer to the open end of the container than is the first layer of thixotropic gel. The solution should have an effective concentration of sodium citrate suitable for preventing coagulation of a sample of blood when such a sample is added to the container. In particular, the solution should have a pH ranging from above 6.0 to about 8.5 and a sodium citrate concentration ranging from about 0.05M to about 0.2M. Additionally, a free space is provided adjacent to the open end of the container for receiving the blood sample and any desired reagents.

The present invention is also directed to a new method for separating monocytes and lymphocytes from heavier phases of a sample of whole blood or, alternatively, from a pretreated cell fraction of blood. A preferred embodiment of the method includes the steps of providing a container having an open end and a closed end. A first layer of a thixotropic gel-like substance is positioned within the container at a first position. An anticoagulant solution prepared in accordance with the present invention and suitable for preventing coagulation of a blood sample is introduced into the container. The solution is positioned at a second position within the container in closer proximity to the open end of the container than the first layer. In particular, the solution includes an effective concentration of sodium citrate suitable for preventing coagulation of a blood sample when such a sample is added to the container. The solution has a pH ranging from above 6.0 to about 8.5. Subsequently, a blood sample is introduced into the container and centrifugation is performed to induce separation of lymphocytes and monocytes from the heavier phases of the blood sample.

As previously mentioned, currently available sodium citrate-based anticoagulant formulations have not provided satisfactory results when used in many of the currently available blood separation/collection containers. This is especially true of blood separation tubes which utilize a thixotropic gel as a barrier or a separation means. In particular, the resulting layer of mononuclear cells appearing after centrifugation is contaminated to an unacceptable level with red blood cells, thereby rendering the separation unacceptable for many applications.

Surprisingly, the sodium citrate solution of the present invention affords a remarkably high recovery (approximately 70–75%) of mononuclear cells when utilized as an anticoagulant in blood separation tubes having thixotropic gel layers incorporated therein. Additionally surprising, is the fact that red blood cell contamination is remarkably low (less than 15%). These recovery and contamination levels are even more surprising in view of the fact that the sodium citrate-based anticoagulant solution has a pH ranging from above 6.0 to about 8.5. This range is approximately 1 to 2 pH points above similar sodium citrate-based solutions used in the past. The effectiveness of the solution of the present invention is indeed surprising since the highest pH at which sodium citrate has been used in the past as an anticoagulant has been 6.0.

Accordingly, the present invention provides an improved sodium citrate-based anticoagulant solution for use in blood chemistry-related techniques and devices, especially blood collection and/or separation assemblies. For a better understanding of the present invention, together with other and further objects, reference is made to the following description, the scope of which will be pointed out in the appended claims.

BRIEF DESCRIPTION OF THE FIGURE

The FIGURE illustrates a sodium citrate-based anticoagulant solution deployed within a blood collection and separation assembly.

DETAILED DESCRIPTION OF THE INVENTION

In accordance with the preferred embodiment of the present invention, a sodium citrate-based anticoagulant solution is prepared in the following manner.

Trisodium citrate.$2H_2O$ and citric acid.$H_2O$ are dissolved in water in amounts sufficient to yield a sodium citrate solution having a desired concentration and pH which fall within the ranges set forth below. For example, a 0.1M sodium citrate solution having a pH of 7.0 (±0.15) can be prepared by dissolving 29.4 grams of $Na_3$ citrate.$2H_2O$ and 0.27 grams of citric acid.$H_2O$ in a liter of $H_2O$.

The concentration of the sodium citrate-based solution should be sufficient for preventing coagulation of a blood sample either added to a blood separation/collection device or involved in some other laboratory/clinical technique. In particular, the concentration of sodium citrate should range from about 0.05M to about 0.2M, and preferably from about 0.08M to about 0.13M. The most preferred range is from about 0.09M to about 0.11M.

Additionally the pH of the final sodium citrate-based solution ranges from above 6.0 to about 8.5, and preferably from about 6.5 to about 7.5. In the most preferred embodiment, the pH ranges from about 6.85 to about 7.15.

Once the solution of the present invention has been prepared according to the aforementioned steps, the solution may be either employed in some laboratory technique or added to any of several blood separation and/or collection tubes available in the art for separating lymphocytes and monocytes from heavier phases of whole blood or a pretreated cell fraction thereof.

While the sodium citrate-based anticoagulant solution of the present invention can be used for any blood separation device, it affords the greatest advantages when used with those devices utilizing a thixotropic gel layer employed either as a cell density separation medium or as a barrier means for isolating various components of the device prior to centrifugation.

In particular, the solution of the present invention can be employed in the construction of an improved blood separation assembly. The preferred embodiment of the assembly includes a container having a closed end and an open end. The container is preferably of the type known in the art capable of collecting a blood sample and undergoing subsequent centrifugation for separation of the sample. Referring to the Figure, a blood collection and separation assembly 10 is shown. The assembly includes a container or tube 12 and a thixotropic gel layer 14 positioned within the tube at a first position.

A variety of thixotropic gels known in the art may be used in the tube depending upon the desired operation to be performed. For example, if the thixotropic gel is employed as a separation medium as well as a barrier means, the gel should have a specific gravity between 1.055 to about 1.080 $g/cm^3$, and preferably a specific gravity of about 1.060 to about 1.065 $g/cm^3$.

If the thixotropic gel is employed in conjunction with a liquid density gradient material, the gel primarily functions as a temporary barrier means prior to centrifugation. In such an assembly, the gel maintains isolation of a blood sample delivered to the tube from the liquid density gradient material residing in the tube until analysis can be performed at a later time. In such a situation, the specific gravity of the thixotropic gel should be within a sufficient range for allowing adequate separation of the mononuclear cell layer from the other components of the blood sample. Preferably, the thixotropic gel employed in such an assembly has a specific gravity ranging from about 1.075 to about 1.085 g/cc. Thixotropic gels are well-known in the art and are typically water insoluble and chemically inert to blood. They are commonly formulated from a dimethyl polysiloxane or polyester and a precipitated methylated silica, wherein the methylation renders the material hydrophobic.

The preferred embodiment of the improved blood separation assembly of the present invention also includes a suitable liquid density separation medium employed within the container at a second position which is further away from the open end of the container than is the thixotropic gel layer. Referring to the FIGURE, liquid density separation medium 16 is shown positioned immediately below thixotropic gel layer 14. Typically, the liquid density separation medium will be of a suitable type known in the art for separating mononuclear cells from whole blood, an example of such being Ficoll-Paque™. In addition to, or as an alternative to the liquid density separation medium mentioned above, a Newtonian gel may be employed within the tube as well.

Finally, the anticoagulant sodium citrate-based solution of the present invention is positioned above the thixotropic gel layer so that it may adequately contact a whole blood sample introduced into the tube for centrifugation and subsequent isolation of the mononuclear cell layer. Referring again to the FIGURE, anticoagulant solution 18 is shown positioned above thixotropic gel layer 14 in closer proximity to the open end of the separation tube 10 than the gel.

As previously mentioned, anticoagulant solution 18 should have an effective concentration of sodium citrate sufficient for preventing coagulation of a sample of blood when such sample is later added to the tube for centrifugation and subsequent analysis. The anticoagulant solution should have a pH ranging from above 6.0 to about 8.5, and preferably from about 6.5 to about 7.5. Most preferably, the pH of the solution should range from about 6.85 to about 7.15. Optimally, the pH should be 7.0.

In the preferred embodiment of the improved blood separation assembly of the present invention, the concentration of sodium citrate should range from about 0.05M to about 0.2M, and preferably from about 0.08M to about 0.13M. Most preferably, the concentration of sodium citrate should be from about 0.09M to about 0.11M. Optimally, the concentration should be 0.1M.

While the anticoagulant solution of the present invention is primarily composed of sodium citrate, additional reagents may be added, such as cell-sustaining solutions or other reagents, in order to provide additional properties to the solution.

The preferred embodiment of the improved blood separation assembly of the present invention also includes a free space adjacent to the open end of the container or tube which is of a sufficient volume to receive a sample of whole blood or a fraction thereof, either alone or in conjunction with an added reagent. In particular, the FIGURE shows free space 20 positioned above anticoagulant solution 16 in order to provide suitable space for accommodation of a blood sample to be separated.

Additionally, the assembly of the present invention may optionally include a closure means for sealing the open end of the container or tube. Typically, the closure means will be suitable for providing vacuum sealing of the open end of the container as well as being pierceable by a needle in order to adapt the container for drawing a sample of blood from a test subject. Referring to the FIGURE, a closure means 22 is provided in the open end of the container or tube for creating a vacuum sealing of the container as mentioned above.

Upon the addition of a blood sample to the assembly 10, mixing of the sample with the anticoagulant solution 18 occurs, typically by manual inversion of the container 12. The thixotropic gel layer 14 remains in a temporarily fixed, first position in the tube to serve as a barrier means for isolating the blood sample/anticoagulant solution suspension from any contact with the other components of the assembly, such as the liquid density separation medium 16.

Upon the subsequent centrifugation of assembly 10, the thixotropic gel layer 14 migrates from the first position toward the top end of container 12. As centrifugation proceeds, the red blood cells separate from the mononuclear cell fraction and become concentrated in a layer immediately above the thixotropic gel. As the thixotropic moves toward a new position within the tube, the red blood cells migrate through the gel to displace the liquid density separation medium below. As the liquid density separation medium is displaced, it moves upward through the thixotropic gel to mix with the mononuclear cell fraction/anticoagulant solution. Red blood cells and granulocytes are pelleted toward the bottom of the tube while the lymphocytes and monocytes form a highly purified mononuclear cell layer immediately above the thixotropic gel layer, thereby facilitating isolation and subsequent removal of the mononuclear cells.

Finally, the present invention includes a method for separating lymphocytes and monocytes from heavier phases of a sample of whole blood or a pretreated cell fraction thereof. The method includes the steps of providing a container having an open and a closed end. Preferably, the container is a blood collection/separation tube of the type mentioned above. The method includes introducing a first layer of a thixotropic gel-like substance into the container or tube at a first position. The method further includes introducing an anticoagulant solution into the container at a second position in closer proximity to the open end of the container than the first thixotropic gel layer. The method also includes the steps of limiting the pH of the solution to any of the preferred ranges previously mentioned as well as the step of introducing the anticoagulant solution of the present invention into the container with an effective concentration of sodium citrate sufficient for preventing coagulation of a blood sample. Additionally, the method includes the step of limiting the concentration of sodium citrate in the solution to any of the ranges previously mentioned in the description of the anticoagulant solution.

The method of the present invention also includes the step of introducing a sample of whole blood or a pretreated cell fraction of blood into the container and the subsequent step of centrifuging the container to induce separation of lymphocytes and monocytes from heavier phases of the sample.

The following Example sets forth performance results for a blood separation assembly employing the sodium citrate solution of the present invention. Accordingly, the following Example serves to provide further appreciation of the invention but is not meant in any way to restrict its effective scope.

EXAMPLE

Forty-five blood specimens from thirty-two healthy adult volunteers were obtained. The blood specimens were from twenty-eight male and seventeen female donors. Blood from each donor was collected into a LeucoPREP™ brand cell separation tube with sodium citrate prepared in accordance with the present invention (Becton Dickinson VACU-TAINER Systems, Prototype Factory Work Order #2324, Lot OL178, exp. November 91, nominal draw volume 4.0 mL) and inverted several times. For subsequent computation of recovery, the actual final volume of blood and citrate was measured with a pipette to the nearest 0.1 mL. Within one hour of blood collection, the tube was centrifuged for 20 minutes at 2280 RPM (1500 xg) (SORVAL RC3C, Du Pont, Wilmington, Del.) at room temperature (25° C., ±1° C.). Following centrifugation, the LeucoPREP™ tube was inverted eight times to resuspend the mononuclear cells in the fluid phase above the gel barrier. The fluid was quantitatively transferred to a 12×75 mm polystyrene round-bottom tube with cap (Becton Dickinson Labware, Lincoln Park, N.J., Catalog #2058). The mean percent recovery of mononuclear cells for the LeucoPREP™ tube containing the sodium citrate solution from this donor population was 71.7% (±10.52). Using a single tailed t-test, the mean percent recovery was shown to be significantly greater than the pre-established minimum acceptable recovery level of 50%. The mean absolute recovery of mononuclear cells using the LeucoPREP™ tube was $6.54 \times 10^6$ ($\pm 1.99 \times 10^6$) cells per tube. The range was 3.36 to $10.54 \times 10^6$ cells per tube. The mean volume of plasma and liquid medium above the gel barrier was 3.2 mL (±0.22), giving a mean cell concentration of $2.04 \times 10^6$ cells per milliliter of cell suspension. The mean recovery of mononuclear cells per mL of whole blood was $1.71 \times 10^6$ from a sample with a mean mononuclear cell count of $2.38 \times 10^6$. The mean purity of the recovered white blood cell suspension was 98.0% (±1.79) mononuclear cells. The LeucoPREP™ results were significantly greater than the pre-established acceptable purity level of 85%. The mean viability of the recovered cell suspension using the LeucoPREP™ tube was 99.9% (±0.27). The mean viability of cells recovered using LeucoPREP™ was significantly greater than the pre-established acceptable minimum of 90%. The mean percentage of red blood cell contamination for the LeucoPREP™ was tube was 14.5% (±9.42).

While there have been described what are presently believed to be the preferred embodiments of the invention disclosed herein, those skilled in the art will realize that changes and modification may be made thereto without departing from the spirit of the invention and it is intended to claim all such changes and modification as fall within the true scope of the invention.

What is claimed is:

1. A method for separating lymphocytes and monocytes from heavier phases of a sample of whole blood or a pretreated cell fraction thereof, said method comprising the steps of:

providing a container having an open end a closed end, said container further having a first layer of a thixotropic gel-like substance contained therein at a first position, said container also having an anticoagulant solution for preventing coagulation of said sample when said sample is introduced into said container, said solution located at a second position within said container in closer proximity to said open end of said container than said first layer, said solution having an effective concentration of sodium citrate and pH adjustor to modify the pH of the sodium citrate anticoagulant solution, sufficient for preventing coagulation of said sample when said sample is added to said container, said solution having an adjusted pH ranging from 6.5 to 8.5;

introducing said sample into said container; and centrifuging said container to induce separation of lymphocytes and monocytes from heavier phases of said sample, wherein the anticoagulant solution affords more efficient cell separation having reduced red blood cell contamination and enhanced recovery and viability of the separated lymphocytes and monocytes.

2. A method according to claim 1, wherein said step of providing said container includes the step of introducing said first layer of said thixotropic gel-like substance into said container at said first position.

3. A method according to claim 1, wherein said step of providing said container includes the step of introducing said anticoagulant solution into said container at a second position within said container in closer proximity to said open end of said container than said first layer and providing said solution with an effective concentration of sodium citrate sufficient for preventing coagulation of said sample.

4. A method according to claim 1, wherein said step of providing said container includes the step of limiting said pH of said solution to a range from about 6.5 to about 7.5.

5. A method according to claim 4, wherein said step of providing said container includes the step of limiting said pH of said solution to a range from about 6.85 to about 7.15.

6. A method according to claim 1, wherein said step of providing said container includes the step of limiting the concentration of sodium citrate to a range from about 0.05M to about 0.20M.

7. A method according to claim 6, wherein said step of providing said container includes the step of limiting the concentration of sodium citrate to a range from about 0.08M to about 0.13M.

8. A method according to claim 1, wherein said step of providing said container includes the step of limiting the concentration of sodium citrate to a range from about 0.09M to about 0.11M.

9. A method according to claim 8, wherein said step of providing said container includes the step of limiting said pH to 7.0 and the step of limiting said concentration of sodium citrate to 0.1M.

10. A method for centrifugally separating lymphocytes and monocytes from heavier phases of a sample of whole blood or a pre-treated cell fraction thereof, said method comprising:

provide a container suitable for centrifugation and having disposed therein a liquid density gradient material, a blood sample and a solution having an adjusted pH ranging from 6.5 to 8.5 and comprising an effective concentration of sodium citrate and pH adjustor to modify the pH of the sodium citrate anticoagulant solution, sufficient for preventing coagulation of said sample; and, centrifuging said container to induce separation of lymphocytes and monocytes from heavier phases of said sample, wherein the anticoagulant solution affords more efficient cell separation having reduced red blood cell contamination and enhanced recovery and viability of the separated lymphocytes and monocytes.

\* \* \* \* \*